United States Patent
King

[19]

[11] Patent Number: 6,051,913
[45] Date of Patent: Apr. 18, 2000

[54] ELECTROACOUSTIC TRANSDUCER AND ACOUSTIC ISOLATOR FOR USE THEREIN

[75] Inventor: Robet W. King, Lexington, Mass.

[73] Assignee: Hewlett-Packard Company, Palo Alto, Calif.

[21] Appl. No.: 09/181,537

[22] Filed: Oct. 28, 1998

[51] Int. Cl.[7] .......................... G01N 29/28; H01L 41/22
[52] U.S. Cl. .......................................... 310/327; 310/322
[58] Field of Search .................... 310/322, 326, 310/327, 334; 29/25.35

[56] References Cited

U.S. PATENT DOCUMENTS

| | | | |
|---|---|---|---|
| 2,881,336 | 4/1959 | Elion | 310/326 |
| 3,403,271 | 9/1968 | Lobdell et al. | 310/326 |
| 3,602,332 | 8/1971 | Hollenbeck | 181/290 |
| 3,663,842 | 5/1972 | Miller | 367/150 |
| 3,794,866 | 2/1974 | McElroy et al. | 310/326 |
| 3,950,660 | 4/1976 | McElroy | 310/326 |
| 4,101,795 | 7/1978 | Fukumoto et al. | 310/336 |
| 4,381,470 | 4/1983 | Leach et al. | 310/327 |
| 4,382,201 | 5/1983 | Trzaskos | 310/327 |
| 4,420,707 | 12/1983 | VanValkenburg | 310/327 |
| 4,433,021 | 2/1984 | Riel | 181/292 |
| 4,434,384 | 2/1984 | Dunrowicz et al. | 310/327 |
| 4,465,725 | 8/1984 | Riel | 181/292 |
| 4,482,835 | 11/1984 | Bar-Cohen et al. | 310/327 |
| 4,504,346 | 3/1985 | Newsam | 181/292 |
| 4,528,652 | 7/1985 | Horner et al. | 367/176 |
| 4,616,152 | 10/1986 | Saito et al. | 310/327 |
| 4,671,841 | 6/1987 | Stephens | 181/292 |
| 4,698,541 | 10/1987 | Bar-Cohen | 367/162 |
| 4,771,205 | 9/1988 | Mequio | 310/327 |
| 4,780,159 | 10/1988 | Riel | 181/292 |
| 4,800,316 | 1/1989 | Ju-Zhen | 310/327 |
| 4,966,799 | 10/1990 | Lucca et al. | 181/290 |
| 4,975,318 | 12/1990 | Suda | 181/157 |
| 5,078,013 | 1/1992 | Kuromachi et al. | 73/620 |
| 5,267,211 | 11/1993 | Miller et al. | 367/176 |
| 5,297,553 | 3/1994 | Sliwa, Jr. et al. | 310/334 |
| 5,309,690 | 5/1994 | Symons | 428/73 |
| 5,325,011 | 6/1994 | Kahn et al. | 310/328 |
| 5,629,906 | 5/1997 | Sudol et al. | 367/162 |
| 5,648,941 | 7/1997 | King | 367/176 |
| 5,670,006 | 9/1997 | Wilfong et al. | 156/236 |
| 5,830,566 | 11/1998 | Kimura et al. | 428/323 |

FOREIGN PATENT DOCUMENTS

| | | | |
|---|---|---|---|
| 54003858A | 1/1979 | Japan | C08K 7/06 |
| 56-85997 | 7/1981 | Japan | 310/326 |
| 06093111A | 4/1994 | Japan | C08J 5/14 |
| 08120095A | 5/1996 | Japan | C08J 5/14 |
| 1 266 143 | 3/1972 | United Kingdom | 310/327 |

*Primary Examiner*—Thomas M. Dougherty

[57] ABSTRACT

An acoustic isolator is formed as a composite of a preform, preferably selected according to a fiber architecture, and an acoustically-attenuating matrix. Fibers in the preform exhibit a first acoustic impedance, and the matrix exhibits a second, lower, acoustic impedance. The preform includes fibers arranged in spaced relationship thus defining a plurality of openings which in turn provide voids that are filled by the matrix. An electroacoustic transducer includes an acoustic pulse generator having a front application face and a rear face mounted on a base having a support structure. The base includes an acoustic absorber attached to the rear face of the pulse generator and the acoustic isolator located between the acoustic absorber and a support structure preferably provided in the form of a heat sink. Preferred embodiments of the preform include linear, planar, and integrated fiber systems; a macroporous mesh structure provided in the form of stacked sheets; or an integrated fiber system; The acoustic isolator prevents a substantial percentage of rear-propagated acoustic energy from traveling between the pulse generator and the support structure, thereby greatly reducing ultrasound display artifacts.

20 Claims, 4 Drawing Sheets

ELECTROACOUSTIC TRANSDUCER AND ACOUSTIC ISOLATOR FOR USE THEREIN

FIELD OF THE INVENTION

This invention relates to improvements in an acoustic isolator, and in particular to an electroacoustic transducer which provides effective attenuation of rear-transmitted acoustic energy.

BACKGROUND OF THE INVENTION

Electroacoustic transducers are generally comprised of an array of active elements in the form of piezoelectric crystals that are mounted in parallel, spaced relationship on the surface of a base of sound-absorbing material. The base is mounted upon a support structure, typically provided in the form of a heat sink. The base is usually constructed of a backing material that exhibits particular acoustical characteristics. The backing material is typically formed by molding a composition of a material having a high acoustical impedance, such as tungsten powder, and an acoustically-absorbing binder so as to substantially eliminate spurious acoustic reflections.

In constructing such a transducer, it is customary (in some applications) to adhere the back of a large crystal to the surface of the base and saw through it in parallel spaced planes so as to form the separate crystals of the array. Acoustic transducer arrays, and in particular ultrasound transducer arrays, may be arranged in a number of configurations including linear, one-dimensional arrays, matrix two dimensional arrays, annular ring arrays, etc. Harmful coupling between the elements of the array by surface waves is substantially reduced by extending the cuts into the base. The base therefore must be precisely cut and exhibits efficient rigidity so as to maintain the crystals in proper position.

It is, therefore, desirable that the base offer certain mechanical and acoustical characteristics: rigidity, for structural support of the elements in an array; selectable acoustic impedance, for controlling or eliminating the reflections at back surfaces of the elements, to achieve a desired balance between output power and image sharpness; and acoustical attenuation, such that acoustic signals exiting the back of the active elements be substantially attenuated so that image-degrading reflections of such signals are not returned to the transducer element.

Figure 1:
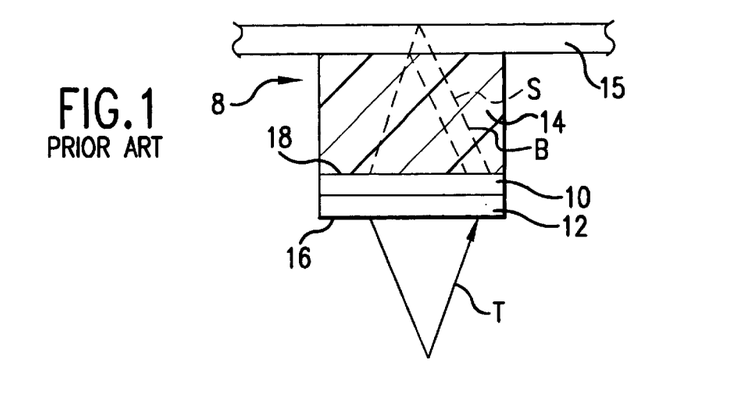
FIG. 1 is a schematic sectional view of a prior art electroacoustic transducer.

Referring to FIG. 1, a schematic of a prior art ultrasound transducer 8 is shown which includes a pulse generator 10 and a matching layer 12 for coupling ultrasound signals into a patient's body. An acoustic absorber backing 14 and a support 15 are positioned behind pulse generator 10. Transducer 8 includes an application face 16 which is placed against the patient's body and from which the principal ultrasound pulses emanate. Pulse generator 10 also propagates pulses through rear face 18 into absorber backing 14. Echoes coming from support 15 are not desired because such echoes appear on the ultrasound display as noise artifacts. As a result, the attenuation rate of absorber backing 14 has to be high to prevent such echoes from appearing on a display screen.

Figure 2:
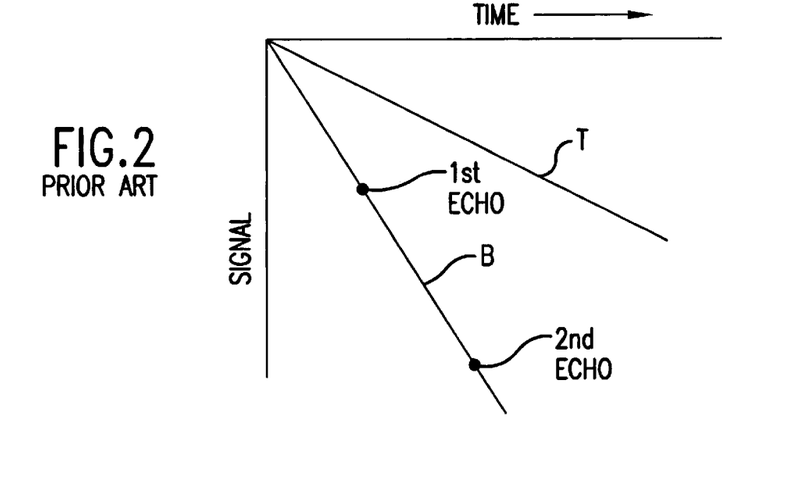
FIG. 2 is a schematic of acoustic signal level versus time, that is useful in explaining the operation of the transducer of FIG. 1.

When a pulse generator 10 is energized, a sound signal T is emitted in a forward direction and is reflected by body tissue, whereas a sound signal B is transmitted in the rearward direction through absorber backing 14, reflected by support 15 and redirected in a forward direction. FIG. 2 is a schematic of reflected signal level vs. time and indicates the size of signal T as reflected from the body tissue vs. the size of the signal in absorber backing B as reflected from support 15. The difference in magnitude in signals T and B is achieved by making the attenuation of absorber backing 14 greater than the attenuation of sound in the body. Note that the sound in absorber backing 14 keeps bouncing back and forth between support 15 and pulse generator 10 until it is entirely absorbed.

It has been found, that when support 15 is attached to absorber backing 14, artifacts sometimes appear on the ultrasound display screen during imaging. This is particularly the case when transducer 8 is thin and when heat sinks (which are relatively thick) are used as backing support. A thin transducer is generally desired in order to make the overall transducer smaller and more easily manipulated.

Due to the lessened thickness of absorber backing 14, the round trip attenuation of sound within absorber backing 14 is lower in thin-aspect-ratio transducers as compared to the thicker variety. This causes more sound energy to be available at pulse generator 10 and thereby causes display artifacts. The attenuation level of absorber backing 14 dictates a minimum thickness transducer 8 which can be made without artifacts. It has also been determined that the shape of a rear-attached heat sink, its placement with respect to absorber backing 14 and the method of mounting the heat sink all effect the amount of displayed artifact. It has been thought that such display artifacts were due to mechanical resonance in the transducer structure and, while various changes in geometry and attachment methods between the heat sink and support body 15 have been tried, some display artifact from rear-reflected signals still remains.

Further analysis of the sound reflective characteristics of transducer 8 in FIG. 1, especially when it is configured as a "thin" transducer, indicate a second source of reflected sound (i.e. signal S) which results from reflections from the back of support 15. Signal S is later in time than signal B due to the increased travel distance through support 15.

Figure 3:
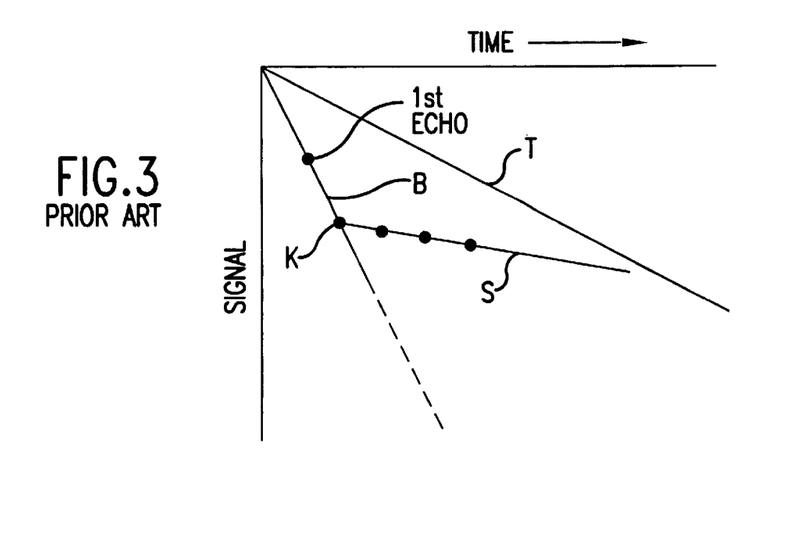
FIG. 3 is a schematic of signal level versus time which indicates the effect of echo reflections from a non-acoustically absorbing support structure.

FIG. 3 is a schematic of signal level at pulse generator 10 as a function of time, considering signals T, B and S. The signal level T from body tissue is the same as described for FIG. 2. The decay rate of signal B from absorber backing 14 is initially slightly higher than that shown in FIG. 2 because some of the initial pulse energy is transmitted into support 15. While signal S is in the support 15 it does not decay with time. Thus, signal S, which comes from the back surface of support 15, decays at a lower rate than signal B (which is entirely in absorber backing 14). This action causes the overall level of signal at pulse generator 10 to decay much more slowly. The knee of curve K corresponds to the time it takes for the first echo S from within support 15 to reach the face of pulse generator 10. That time is proportional to the thickness of acoustic absorber backing 14. The slope of curve portion S, i.e. the decay rate of echoes from within support 15, is determined by the ratio of the thickness of support 15 divided by the thickness of absorber backing 14. Thus, the thicker is support 15 and the thinner is absorber backing 14, the more display artifact is present. The geometry is also important. If support 15 is wider than the backing (as shown in FIG. 1), the slope of S is also reduced.

Sudol et al., in U.S. Pat. No. 5,629,906, disclose an acoustic transducer having a support structure which holds an acoustic pulse generator. An acoustic absorber is attached to the rear face of the pulse generator. An acoustic isolator is positioned between the acoustic absorber and a support structure/heat sink. The acoustic isolator includes at least a first material layer exhibiting a first acoustic impedance value, and a second material layer exhibiting a second acoustic impedance value. The second acoustic impedance value is substantially different from the first acoustic impedance value. A boundary between the first material layer and the second material layer causes multiple acoustic reflections of an acoustic pulse emanating from the rear face of the pulse generator. The acoustic isolator acts as a multiple reflective layer and prevents a substantial percentage of rear propagated acoustic energy from entering and being reflected by the support structure, thereby reducing ultrasound display artifacts.

However, Sudol teaches that each material layer be bonded directly to an adjacent material layer without intervening adhesive or other non-thermally conductive material, and a diffusion bonding process be employed. Such a bond is expensive and difficult to achieve in a consistent and defect-free manner. Furthermore, such a technique can be subject to the inclusion of undesirable air pockets, each of which can reflect acoustic energy and accordingly cause image artifacts. Extensive testing of each assembly may be required to confirm that few or non of such pockets are present.

Accordingly, the advent of ever-smaller ultrasonic transducers continues to impose a need for highly-attenuating base wherein the thickness of the base is reduced. However, it has proven difficult to achieve a base that, in addition to providing adequate structural support, can be constructed to exacting tolerances as a thin member, is highly attenuating, and is easily constructed without defects. Certain transducer arrays are useful for some applications if constructed to dimensions that are more exacting than those made possible by conventional methods.

There remains a need for a thin aspect ratio ultrasound transducer which exhibits excellent heat dissipation properties, is susceptible to formation to close tolerances by use of precision forming techniques, such as high-speed milling or electrical discharge methods (EDM), and nonetheless provides effective attenuation of rear-transmitted acoustic energy.

SUMMARY OF THE INVENTION

The present invention is directed to a novel acoustic isolator, and to a novel construction of an electroacoustic transducer having a base formed of the acoustic absorber and an acoustic isolator. The acoustic isolator is preferably constructed as a component or a layer attached to a support structure, wherein the acoustic isolator includes therein a composite having a fibrous structure to promote scattering, i.e., multiple internal reflections, of acoustic energy, and an attenuating matrix which traps and attenuates the scattered acoustic energy, so as to prevent a substantial percentage of acoustic energy entering the acoustic isolator from being transferred to, and subsequently being reflected by, a contiguous boundary between the acoustic isolator and the support structure.

A preferred embodiment of the electroacoustic transducer includes a base which supports an acoustic pulse generator having both a front application face and a rear face. An embodiment of the above-described acoustic absorber is attached to the rear face of the pulse generator. The acoustic isolator is positioned between a rear surface of the acoustic absorber and a forward surface of the support structure. The acoustic transducer thereby benefits from a substantial reduction in the acoustic energy coupled between the acoustic absorber and the support structure, thereby reducing the amount of acoustic energy reflected from the support structure to the pulse generator, thus reducing ultrasound display artifacts.

A preferred embodiment of the acoustic isolator includes a composite formed of a preform, selected according to a predetermined fiber architecture, and a matrix formed of an acoustically absorbing binder material. The preform is composed of fibers exhibiting a first acoustic impedance value, and the matrix is composed of a binder exhibiting a second acoustic impedance value. The second acoustic impedance value is substantially lower than the first acoustic impedance value. The preform includes fibers arranged in a predetermined relationship so as to create a plurality of voids which are substantially filled by the binder material during construction of the composite. The fibers in the preform scatter incident acoustical energy, thus causing acoustical attenuation of the acoustical energy within the matrix, wherein "attenuation" is defined herein as a reduction of acoustical energy by a combination of one or more of: absorption, diffraction, interference, and dispersion.

In a particularly preferred embodiment, the preform is composed of a stacked arrangement of metallic cloth sheets. A preferred metallic cloth sheet may be provided in the form of tungsten fiber cloth.

In another particularly preferred embodiment, the binder material is composed of a thermosetting epoxy resin selected for its acoustical attenuation characteristic.

In another preferred embodiment of the acoustic isolator, the binder offers enhanced thermal and electrical conductivity. The matrix accordingly includes an additive, such as silver, that exhibits substantial electrical conductivity and heat transfer capabilities.

In a particularly preferred method, the acoustic isolator is provided according to the steps of: arranging a stacked array of metallic fiber cloth sheets interleaved with B-staged epoxy films, subjecting the array to a compression force to compress the array to a predetermined first stacked height, heating the compressed array to a pre-cure temperature, maintaining the first stacked height in the compressed array at a pre-cure temperature for a predetermined time, adjusting the compression force on the array to achieve a second stack height, maintaining the array at a cure temperature for a predetermined period to cure the array; and relieving the compression force and cooling the array to provide a finished component suitable for use as the acoustic isolator.

One feature of this invention is that the composite can be tailored to satisfy a combination of desired mechanical strength, thermal and electrical conductivity, acoustical attenuation, and precisely-defined dimensions and other physical requirements.

In another feature of the present invention, the preform is provided according to at least one of a plurality of a fiber systems in a fiber architecture in which the fibers are arranged and oriented in a predetermined fashion. An advantage of the contemplated preform is that it is easily formed by known textile manufacturing techniques to form an "open" or porous structure having a plurality of voids, which may be uniformly or variably spaced, such that the matrix material can easily fill substantially all of the voids by techniques such as injection molding, compression molding, or vacuum-impregnation. Furthermore, the composite can be constructed to satisfy a predetermined, nonlinear amount of acoustic attenuation either isotropically or directionally in any of the three orthogonal axes.

In a preferred embodiment of the present invention, the preform is provided according to a planar fiber system in which the fibers are oriented in a stacked (i.e., multi-layer) macroporous mesh structure. The preferred embodiment of the mesh structure employs macroporous mesh materials in the form of precut macroporous mesh sheets. Such sheets are contemplated as including generally uniformly sized and spaced filaments arranged such that when the mesh sheets are overlaid (i.e., stacked), a plurality of macro-scale voids are uniformly distributed in the resulting mesh structure. One can also select the acoustic velocities, impedances, and attenuation characteristics of the acoustic isolator by stacking layers of sheets having differing porosity and then injection molding or vacuum-impregnating an appropriate resin into the stack.

In another preferred embodiment, the preform includes a stacked arrangement of macroporous mesh sheets, wherein each macroporous mesh sheet is formed of a plurality of tungsten mono-filaments, interleaved with one or more layers of B-staged epoxy film. The stacked arrangement of sheets is subject to compression force to achieve a selected stack height, and subjected to a cure temperature for a predetermined period to cure the layers of epoxy film. After relieving the compression force and cooling the stack, the finished component is suitable for use as an acoustic isolator.

In another embodiment of the present invention, the fiber preform is selected from an integrated fiber system in which the fibers are oriented in various in-plane and out-of-plane directions according to a three-dimensional network of fiber bundles formed in an integral manner. The integrated structure allows additional reinforcement in the through-thickness direction, which makes the composite virtually free of delamination. Another useful aspect of a fully integrated fiber structure, such as three-dimensional woven, knit, or braid, is an ability of the composite structure to assume a complex structural shape.

The binder material is preferably selected from a range of known, acoustically-attenuating, curable (e.g., thermosetting) materials, such as epoxy resin or polyvinyl chloride. Additives, such as such as tungsten powder for increased density, or other powdered materials such as powdered silver for effecting improved thermal and electrical conductivity, are easily incorporated into the matrix, as their particle size is small enough to allow uniform dispersion throughout the composite. By selecting a preform of variable porosity, and a having fibers of one or more differing compositions, e.g., metallic fibers such as tungsten, copper, stainless-steel, or as mineral or ceramic fibers, the acoustic isolator may be provided with selectable physical, mechanical, and acoustical properties.

In another aspect of the present invention, the composite may employ a binder material selected from certain useful, highly acoustically-attenuating materials that otherwise are not sufficiently rigid or machinable for use as in a transducer, and thus heretofore have not found advantageous use in an acoustic isolator, and especially in an acoustic isolator provided in an electroacoustic transducer.

DETAILED DESCRIPTION OF THE PREFERRED EMBODIMENTS

It has been found that if an acoustic pulse emanating from the rear face of an acoustic transducer encounters an acoustic isolator which isolates the incident energy before it can reach a non-attenuating support, the display artifacts maybe reduced or eliminated. See Sudol et al., in U.S. Pat. No. 5,629,906 (the contents of which are incorporated herein by reference), wherein an acoustic isolator is described as providing multiple reflective layers between an acoustic absorber and the non-attenuating support.

As is known to those skilled in the art, the acoustic impedance Z of a propagating medium is the product of the density of a medium and the speed of sound through the medium. For example, the acoustic impedance for various materials indicates that tungsten carbide, tungsten, stainless-steel, molybdenum, and nickel exhibit relatively high acoustic impedances; the acoustic impedance for various other materials indicates that resins, polymers, synthetic and natural rubbers, and the like exhibit relatively low acoustic impedances.

As will now be described, a novel acoustic isolator suitable for use in a preferred embodiment of a novel electroacoustic transducer constructed according to the present invention includes a fiber preform that includes fibers having a first acoustic impedance and an interspersed matrix having a second, substantially lower acoustic impedance. The resulting composite structure effects substantial internal scattering of incident acoustic waves and substantial attenuation of the scattered acoustic waves due to dispersion, absorption, and the like within the matrix.

Figure 4:
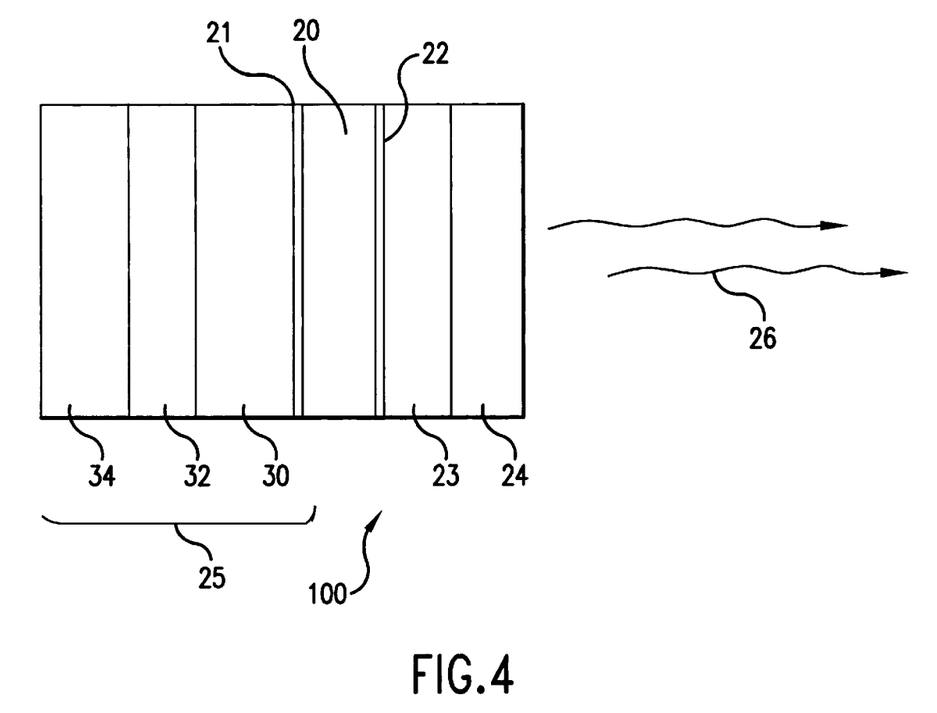
FIG. 4 is a side sectional schematic view of a novel electroacoustic transducer having a novel acoustic isolator constructed in accordance with the teachings of this invention.

FIG. 4 illustrates the principal components of a preferred embodiment of an electroacoustic transducer 100 shown in section. An array 20 of active elements, shown in section, transmits and receives acoustic beams formed by, e.g., the switching of each element in a phased array format. The elements are preferably formed of piezoelectric crystals and there may be a single one or a plurality of electrically-independent active elements in the array 20. A first electrode layer 22 overlying and a second electrode layer 21 underlying each active element enables the element to be individually and electrically addressed. A base 25 constructed according to the present invention provides structural support for the array 20 and associated electrodes 21, 22. An acoustic matching layer 23 may be included to provide an acoustic impedance transition between the array 20 and an optional acoustic lens 24. The desired emission 26 of the transducer 100 is considered as emanating from the "forward" or foremost side of the transducer 100; the base 25 and the ancillary components attached to the base 25 (such components being a housing and the like, which are omitted for clarity) are generally considered as located at the "rear" or backside of the transducer 100. A similar convention in nomenclature will apply to the intervening elements, e.g. the foremost or "active" surface of the array 20 is coupled to the rear surface of first electrode layer 22; the rear surface of the transducer array 20 is coupled to the second electrode layer 21. The array 20 is typically subject to unwanted, rear-transmitted acoustical emissions that emanate from the backside of the array 20 and into the base 25.

Accordingly, and as shown in FIG. 4, the base 25 includes an acoustic absorber 30 formed of an appropriate transducer backing material selected from those known in the art. The base 25 also includes a preferred embodiment of an acoustic isolator 32 which is interposed between a back surface of the acoustic absorber 30 and a non-attenuating layer 34 (which may be a support structure, a heat sink or a combination thereof).

The acoustic isolator 32 preferred for use in the base 25 is formed as a composite of a fiber structure preform having a first acoustic impedance in a composite with a matrix having an interspersed binder having a second, substantially lower acoustic impedance, and wherein the composite exhibits useful characteristics of acoustic wave scattering, structural strength, rigidity, and ease of manufacture. Preferred embodiments of the acoustic isolator 32 also include first and second thin metallic surface coatings respectively on the foremost and rearmost surfaces, which aid in the assembly and bonding of the acoustic isolator 32 with the other components of the base 25, and improve the matching of acoustic impedances between the acoustic isolator 32 and the immediately contiguous back surface of the acoustical absorber 30. Suitable metallic surface coatings include copper, gold, and the like.

Figure 5:
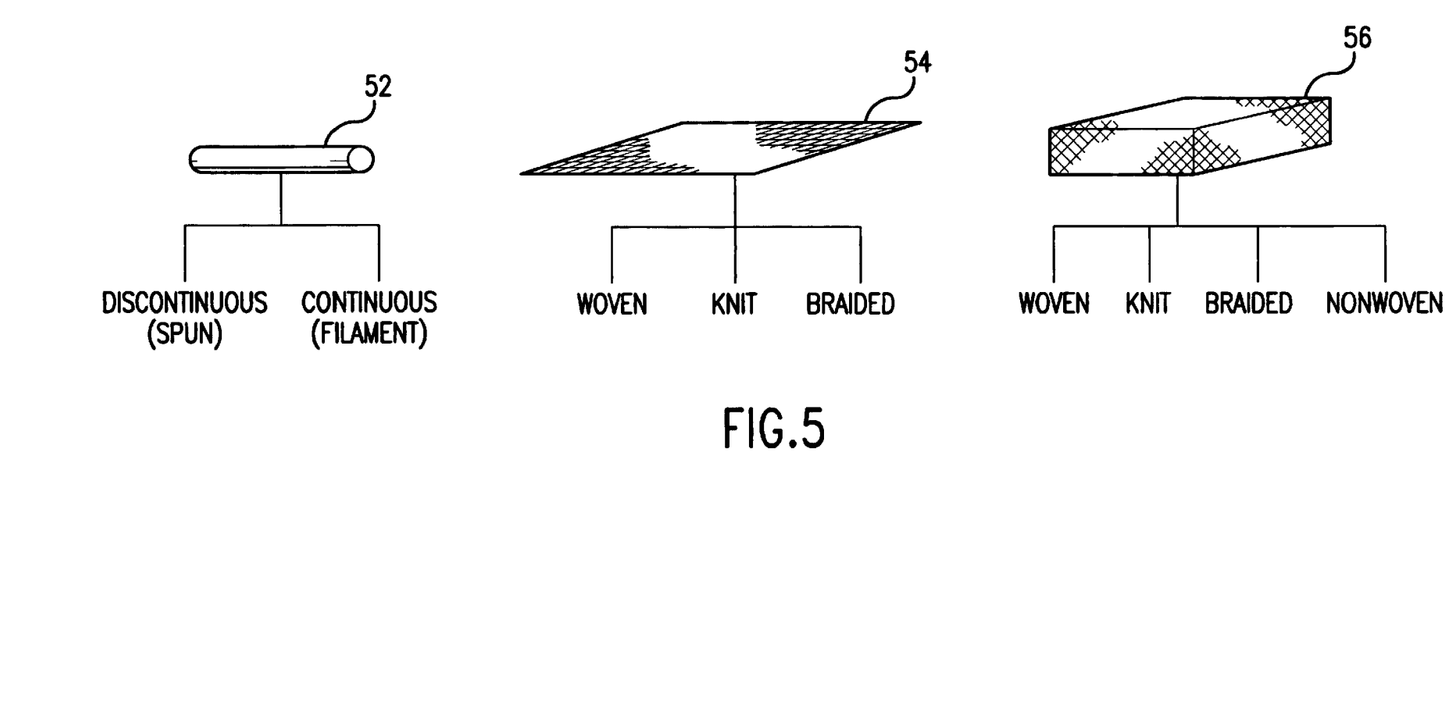
FIG. 5 is a diagrammatic representation of a fiber architecture system from which a preform may be selected for constructing the acoustic isolator preferred for use in the electroacoustic transducer of FIG. 4.

The relatively high acoustic impedance of the fiber structure in the acoustic isolator 32 is provided by selection of appropriate materials for a fibrous preform, examples of which are illustrated in FIG. 5. Preferred examples of the fibrous preform include macro-porous sheets of plural tungsten fibers, or of other metallic fiber architectures, as discussed below. Preferred examples of starting materials for the binder include a thermosetting resin, such as an epoxy material, and a particularly preferred example includes a partially cured (also known as partially cross-linked, or "B-staged") epoxy film or sheet that may be interleaved between the macro porous tungsten fiber sheets.

For the purposes of this description, the acoustic impedance indicated by a first, or "high" acoustic impedance, preferably exceeds a second, or "low" acoustic impedance by a factor in the range of 5 to 20. For example, a preferred tungsten fiber preform exhibits an acoustic impedance of approximately 30 MRayls, whereas a preferred matrix having an epoxy binder therein exhibits an acoustic impedance of approximately 1.7 to 2.0 Mrayls.

Figure 6:
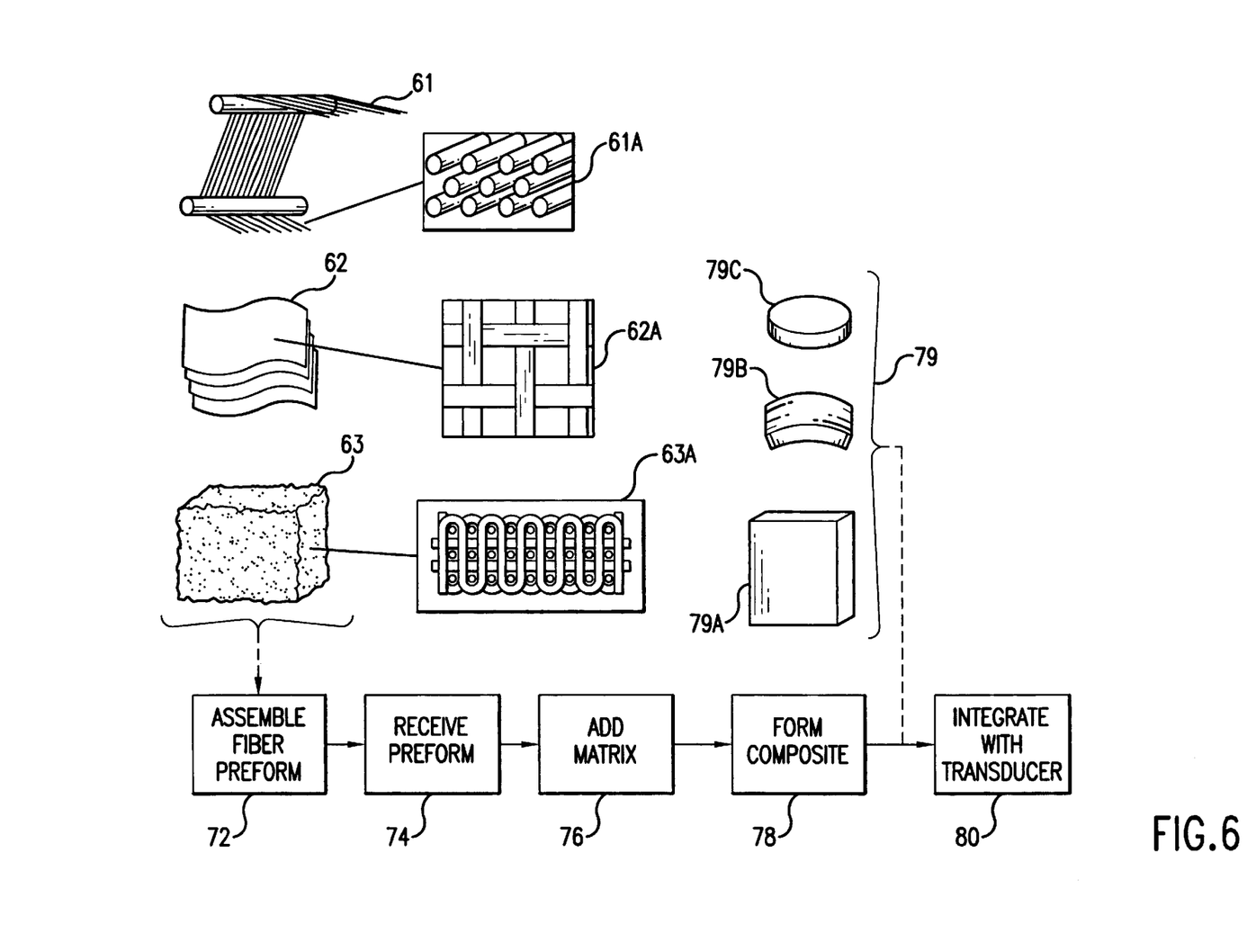
FIG. 6 is a diagrammatic representation of a method of constructing the acoustic isolator of FIG. 4, with exploded views of preferred preforms and composite structures provided according to the invention.

With reference to FIGS. 5 and 6, the present invention is therefore directed to an acoustic isolator 30 preferred for use in the base 25 that is formed as a composite of a fiber preform and a matrix having a binder material for scattering and acoustical attenuation of unwanted acoustic energy received by the base 25. Preferred embodiments of the composite may be constructed according to a variety of techniques, including a preferred method wherein a preform is filled with a suitable binder such as plastic, resin, or other solutions to form the composite; the resulting composite may be formed via materials process techniques as a continuous ribbon, cylinder, etc. of acoustic isolator stock material (e.g., in a bulk form) or as one or more composite component forms via known manufacturing techniques such as pultrusion, molding (e.g., injection molding or compression molding), and/or hardening by thermosetting, chemical reaction, or ultraviolet curing, etc.. A composite structure may thus be provided in a preferred form factor, or be machined to the desired shape, so as to be easily integrated into the transducer 100.

As shown in FIG. 5, the preform is preferably selected from a fiber architecture that includes a linear fiber system 52, a planar (also known as laminar or two-dimensional) fiber system 54, and an integrated (also known as three-dimensional) fiber system 56. As shown, each fiber system may be embodied in a fiber preform type such as woven, knit, and braided, etc.; further description herein of these fiber systems may be understood according to terminology known in the textile arts. In particular, a preform is defined as a fibrous structure for use in a composite structure before matrix introduction. A fabric is defined as an integrated fibrous structure produced by fiber entanglement or yarn interlacing, interlooping, intertwining, or multiaxial placement. A fiber-to-fabric structure is a fibrous structure manufactured directly from fibers into a fabric (e.g., felt, fiber mats). Fiber felts, where the fabrics are formed directly from fibers, and a multiaxial warp knit (a warp-knitted fabric with yarns of a certain orientation assembled with stitching yarns oriented in the through-thickness direction) are examples of fiber-to-fabric structures. A yarn comprises a linear fibrous assembly consisting of multiple filaments. A yarn-to-fabric structure is a fabric structure constructed from yarns by a weaving, knitting, non-woven, or braiding process. For example, the process of weaving is a fabric-formation process using the interlacing of yarns. Woven fabric combinations are made by interlacing yarns; knitted fabrics are interlooped structures in which the knitting loops are produced by introducing the knitting yarn either in the cross-machine direction (weft knit) or along the machine direction (warp knit). Braided fabrics can be produced in flat or tubular form by intertwining three or more yarn systems together. Further details on the illustrated fiber architecture may be found in Ko, in "PREFORM FIBER ARCHITECTURE FOR CERAMIC-MATRIX COMPOSITES", *Ceramic Bulletin,* Vol. 68, No. 2, 1989.

On the basis of structural integrity and fiber linearity and continuity, the preform may be selected from one of four levels of reinforcement systems: discrete fiber, continuous filament, laminar (including planar interlaced, interlooped, or other two-dimensional system), or fully integrated (three-dimensional). Some properties of these four levels are summarized in Table 1 according to Scardino in *Introduction to Textile Structures;* Elsevier, Essex, UK, 1989. For example, as the level of fiber integration increases (from I to IV), the opportunity for fiber-to-fiber contact increases at the fiber crossover points.

TABLE 1

| | | Fiber Architecture Levels | | |
|---|---|---|---|---|
| Reinforcement System Level | Textile Construction | Fiber Length | Fiber Orientation | Fiber Entanglement |
| I | Discrete | Chopped fiber | Discontinuous | Uncontrolled | None |
| II | Linear | Filament yarn | Continuous | Linear | None |

TABLE 1-continued

| | | Fiber Architecture Levels | | | |
|---|---|---|---|---|---|
| | Reinforcement System Level | Textile Construction | Fiber Length | Fiber Orientation | Fiber Entanglement |
| III | Laminar | Simple fabric | Continuous | Planar | Planar |
| IV | Integrated | Advanced fabric | Continuous | 3-dimensional | 3-dimensional |

The first level is the discrete-fiber system which includes fiber structures that comprise discontinuous or continuous fibers. The structural integrity of such a fiber structure is derived mainly from inter-fiber friction.

The second level is the linear fiber system. This architecture has the highest level of fiber continuity and linearity and, consequently, has the highest level of property translation efficiency and is suitable for filament wound and angle-ply tape layup structures. The drawback of this level of fiber architecture is its intra-laminar and inter-laminar weakness due to the lack of in-plane and out-of-plane yarn interlacings.

The third level is the laminar fiber system having, e.g., planar interlaced and interlooped systems. Although the intra-laminar failure problem associated with the continuous filament system may be addressed with this fiber architecture, the inter-laminar strength is limited by the matrix strength due to the lack of through-thickness fiber reinforcement.

The fourth level, an integrated fiber system, includes fibers oriented in various in-plane and out-of-plane directions. For example, with use of continuous filament yarn, a three-dimensional network of yarn bundles may be formed in an integral manner. The integrated fiber system affords additional reinforcement in the through-thickness direction, which causes the resulting composite to be virtually free of undesirable delamination. A fully integrated structure, such as three-dimensional woven, knitted, or braided preform can assume complex structural shapes.

Preferred embodiments of acoustic isolator 32 that utilize discrete or linear fiber preforms may have insufficient strength between a given fiber or fiber layer, and the adjacent fibers or fiber layers. Also, in the planar fiber system, the fiber reinforcement effectively occurs in one plane only and is greatest within this plane in the one or two directions parallel to the fiber orientation. Little or no reinforcement is present in the direction perpendicular to the fiber plane.

Accordingly, while preforms selected from levels I and II of the Table are suitable for use in the preferred composite, a particularly preferred embodiment will incorporate a preform composed of fiber system selected to include a level III fiber system.

The preferred composite for the acoustic isolator 32 shown in FIG. 4 and described with reference to FIG. 5 may be provided as illustrated in the process shown in FIG. 6. Illustrated are linear, planar, and fully integrated preforms 61, 62, or 63, one of which may be assembled in a fiber preform assembly step 72. For example, a plurality of macroporous tungsten mesh sheets can be stacked together to form a laminar preform 62. Preferred mesh sheets have a mesh range of 5 mesh to 200 mesh and a wire diameter of 0.0005 to 0.010 inches, and most preferably approximately 150 mesh with a wire diameter of 0.0008 inches. Additional procedures such as compression, interlacing, trimming, and the like of the preform 61–63 may also be performed in step 74. For example, one preferred bonding procedure in steps 74 or 74 includes compressing or tensioning of the preform 61–63 so as to alter the spacing between adjacent fibers. The preform is then bonded with a matrix material in step 76 to form a composite 79 in step 78 according to a predetermined form factor, such as an orthogonal slab 79A, a curvilinear slab 79B, or disc 79C, so as to provide the acoustic isolator 32 of FIG. 4. The steps 74–78 may utilize techniques known, e.g., in the injection molding, compression molding, thermosetting, and other plastic fabrication arts. Alternatively, the composite may be formed into a bulk, and suitable form factors may be provided by EDM, cutting, machining, and sizing techniques to form the desired shape for the acoustic isolator 32.

Other shapes and/or form factors of the composite 79 as well as other techniques for forming various types of the composite are contemplated and could be utilized as appropriate, as would be apparent to those skilled in the art.

In particular feature of the present invention, and as illustrated by the exploded portion 62A of the mesh sheet 62, the individual fibers of the preform are arranged in a predetermined spaced relationship so as to act as acoustical energy scatterers. The scattered energy is then believed to be attenuated by interference and dispersion effects.

In another particular feature of the present invention, the minute voids presented by the spaced fibers are substantially filled with a matrix selected for its acoustically-attenuating properties, whereby the interstitial volumes of matrix thereby function as attenuating traps for the scattered acoustic energy. In such an embodiment, the scattered acoustical energy is not only subject to interference and dispersion, but also absorption within the matrix. Because the average size and spacing of the voids is easily and inexpensively defined during manufacture of the preform in the assembly step 72 (such as by the selection of the filament spacing during manufacture of the mesh sheets 62), the success of the resulting composite 79 is not dependent upon the requirements for proper dispersion of, e.g., high acoustic impedance powders, particles, and the like, such as are taught in the prior art. As a result, the composite 79 offers not only rigidity, but also excellent wave scattering and acoustic energy attenuation.

In embodiments which utilize a stacked or layered arrangement of fibers (such as in preforms 61, 62), the layers or sheets of fibers can be inter-leaved with binder provided in the form of thin, pre-cured film sheets, whereby be layered arrangement can be subject to compression and a final curing step so as to be cast in the desired form factor, or be arranged in a mold or form which is then filled and cured by, e.g., injection molding techniques, with the binder material. Other possibilities include feeding an arrangement of multiply overlaid fibers or fibrous sheets into a slip form, which form is continuously or periodically filled with a liquid matrix. The resulting bulk form of the composite can then be processed further, such as by curing and slicing to the desired size and shape of the acoustic isolator 32. Still another option may be to alternatively lay fibrous sheets on layers of epoxy loaded with acoustic absorbers; a stack is built up of alternating layers until the desired number of fibers are reached and the epoxy is then given a final cure. Still another option may be to lay fibrous sheets having therein high acoustical impedance fibers already loaded with epoxy or a similar acoustic absorber material distributed in plural inter-fiber or interstitial segments of the fibrous sheets; a stack is built up of the desired number of layers; the stack may be compressed until the desired stack height is reached and the arrangement is then subject to an elevated temperature and given a final cure.

An integrated (three-dimensional) fiber preform 63 affords three-dimensional integrity in all three axes. The matrix material is added for setting the filaments in their preselected orientation, and for enhancing the acoustical, physical, thermal, ablative, and other properties of the preform. The basic strength of the preform results primarily from inter-yarn friction of the adjacent filaments, where they intersect throughout the material. This friction provides the binding forces which can maintain fabric integrity even in the absence of the matrix.

The present invention also contemplates that the dynamics of the interaction between the forming process and the resulting composite structure allows one to select an optimum pore geometry, pore distribution, and fiber bundle size. A three-dimensional architecture with a regular fiber network of interlacings thus provides a stable preform for the infiltration and deposition of a matrix under high temperatures. An integrated fiber preform 63 also provides through-thickness reinforcement. Accordingly, a high level of flexural strength can be attained with a composite formed by use of the integrated preform 63.

The preferred preforms 61–63 may be provided with fiber spacing, sizes, density, etc. that varies spatially across one or more axes of the preform. For example, the density of fibers of one size being much greater than the density of fibers of other sizes. The fibers supplied to the composite during the steps 72, 74 may contain fibers predominantly of one size but also contain smaller fibers. It would also be possible, but not necessary, to arrange for the size of the fibers to gradually increase with the distance from the foremost surface of the acoustic isolator 32.

According to another feature of the present invention, the reinforcement density and stiffness in each axis of the composite structure can be varied independently of another axis by using different fiber sizes, densities, and groupings and also by changing fiber compositions. Examples of suitable fibers include metallic fibers such as tungsten, stainless-steel, and nickel; metal-on-metal fibers such as a tungsten fiber core coated with gold, nickel, and the like; metal-clad fibers, such as a graphite fiber core coated with nickel, gold, and the like; and ceramic fibers and similar filamentary materials such as carbon, graphite, or quartz filaments. In addition, the composition and orientation of these fibers in the composite structure can be varied to control the acoustical, physical, and mechanical properties of the acoustic isolator. In particular, the characteristics of the preform and the matrix can be controlled through these variables to provide materials having precisely the properties required for the particular application.

It is also contemplated that at least one embodiment may utilize electrically and thermally conductive particles, such as silver particles, as an additive dispersed in the composite for enhancing thermal and electrical conductivity as already described herein.

It is contemplated that the acoustic isolator 32 is constructed such that there is little or no secondary coupling of acoustical energy from the matrix to the fibers in the preform. If such coupling occurs, the acoustic properties of interest in removing any acoustic energy from the fibers (resulting in the energy being better attenuated in the acoustic isolator 32) are the relative acoustic impedances of the materials for the fibers and the relative acoustic velocities of such matrix materials as mentioned herein. In particular, as indicated above, an impedance match between the fibers and the matrix would facilitate flow of acoustic energy from the filaments into the binder. To further facilitate this process, it is contemplated that the acoustic impedance of the fibers be significantly greater than the acoustic impedance of the matrix, or of at least a portion of the matrix surrounding the fibers. This results in the composite better functioning as a trapping matrix, so that acoustic energy is directed out of the fibers rather than being directed back into the fibers and propagated therein. A desired difference in acoustic impedance may be alternatively obtained wherein the binder is formed of a material having a lower acoustic impedance than the filaments. Also by providing fibers of decreasing acoustic velocity extending out from the forward surface of the acoustic isolator 32 in conjunction with acoustic impedance matches in the layer 30, one may couple much of the acoustic energy from array 20 into acoustic isolator 32, such energy being attenuated therein.

In general, therefore, reflections from, e.g. the rear surface of the acoustic isolator 32 can be thus substantially eliminated, thus preventing reflections returned to the array 20 that may cause degradation in the image quality of the transducer 100.

Reflections of acoustic energy, if any, at the foremost layers of the fibers to the array 20 may be circumvented by, e.g., including sufficient binder at such junction in a sufficient thickness to substantially attenuate acoustic energy coupled therein, or, in composites utilizing preforms of variable porosities, by the placement of fibers at the forward portion of the acoustic isolator 32 having a differing porosity in comparison to the fibers placed at the rear of the acoustic isolator 32. To the extent any acoustic energy may be reflected from a foremost sheet at the forward portion of the acoustic isolator 32, such energy is fully or near fully attenuated in its two passes through the adjacent, foremost layer of acoustic absorber 30.

Preferably, one or more impedance transition or impedance matching layers are be provided in the acoustic isolator 32 to minimize reflections at the forward portion of the acoustic isolator 32; the construction of the composite may be gradually varied over an intermediate region of the acoustic isolator 32 so that there is no sharp reflection-causing acoustic impedance transition. Thus, by gradually varying the acoustic impedance across the depth of acoustic isolator 32 or by some combination of the aforementioned techniques, a near optimization of acoustic attenuation may be achieved so as to minimize acoustic reflections.

One advantage of the invention is the provision of a base 25 useful for fabrication of miniature electroacoustic transducers without compromising acoustical performance and at the same time enabling reliability and ease of manufacture.

Another advantage of the invention is the provision of an acoustic isolator 32 that is very light in weight, has high acoustic attenuation, minimal acoustic back scattering, substantial structural integrity, thermal stability, high permeability (which permits vacuum evacuation and backfilling), and superior adhesion because of its ability to be machined smoothly and cleanly.

A further advantage of the invention is the provision of a base 25 that may be formed in an appropriate form factor, or exhibit sufficient elasticity, so as to be bent across a gentle radius for shaping curvilinear arrays.

One further advantage of the invention is the provision of an electroacoustic transducer that has a high degree of acoustical attenuation in a rigid base 25 that nonetheless it is susceptible to exacting fabrication techniques such as EDM, milling, kerfing, dicing, and other transducer manufacturing procedures. The contemplated electroacoustic transducer 100 can be reliably reproduced in mass manufacturing methods while offering such features as a very thin profile.

The present invention utilizes a preform to provide the rigidity necessary to fabricate a multi-element transducer array and to maintain planarity of the array. Thus, another advantage of the invention is that certain binder materials may now be effectively used in the thickness necessary for miniaturization and ease of manufacture, that heretofore were unsuitable for use in a transducer. For example, such materials may offer next wants acoustic attenuation but are otherwise be unsuitable because they lack of the requisite mechanical rigidity when provided in a thickness of a millimeter to a few millimeters. Such materials include certain rubber, polymer, or other natural or synthetic formulations that can attenuate well in minimal thickness but have little structural integrity.

While the invention has been particularly shown and described above with reference to preferred embodiments, it is apparent that the foregoing and other changes may be made in form and detail by one skilled in the art while still remaining within the spirit and scope of the invention.

What is claimed is:

1. An acoustic isolator for use in an electroacoustic transducer, comprising:
    a composite formed of a preform and a matrix, wherein the preform includes fibers arranged in spaced relationship so as to define a plurality of voids, said voids being substantially filled by a binder, wherein the fibers exhibit a first acoustical impedance and said matrix exhibits a second, lower acoustical impedance, wherein the first acoustical impedance and the second acoustical impedance are selected such that acoustical energy received by said composite is subject to scattering by said fibers and attenuation in said matrix.

2. The acoustic isolator of claim 1, wherein the fibers are selected from a group of fiber materials consisting of: metallic fibers; metal-on-metal fibers; metal-clad fibers; ceramic fibers, and filamentary materials.

3. The acoustic isolator of claim 1, wherein said binder is provided in the matrix by a technique selected from the group consisting of: injection, pultrusion, compression molding, slip-forming, and vacuum-impregnation.

4. The acoustic isolator of claim 1, wherein said binder is selected from a group of binder materials consisting of: thermoplastic polymers and thermosetting resins.

5. The acoustic isolator of claim 1, wherein said preform comprises spaced fibers arranged according to a predetermined fiber architecture, said fiber architecture being selected from the group consisting of: linear fiber system; planar fiber system, and integrated fiber system.

6. The acoustic isolator of claim 5, wherein said preform further comprises stacked layers of macroporous metallic mesh sheets.

7. The acoustic isolator of claim 6, wherein said mesh sheets comprise tungsten filaments.

8. The acoustic isolator of claim 6, wherein said mesh sheets have a mesh range of 5 mesh to 200 mesh and a wire diameter of 0.0005 to 0.010 inches.

9. The acoustic isolator of claim 6, wherein said matrix is comprised of an epoxy resin.

10. The acoustic isolator of claim 1, wherein said matrix further comprises an additive having a physical characteristic selected from a group consisting of: thermally conductive and electrically conductive.

11. The acoustic isolator of claim 10, wherein the matrix further comprises silver-filled epoxy.

12. An electroacoustic transducer, comprising:
    a base having a support structure, an acoustic absorber, and an acoustic isolator;
    an acoustic pulse generator having both a front application face and a rear face, wherein the acoustic absorber is attached to the rear face of the pulse generator and the acoustic isolator is positioned between the acoustic absorber and the support structure;
    wherein the acoustic isolator includes a composite formed of a preform and a matrix, wherein the preform includes fibers arranged in spaced relationship so as to define a plurality of voids, said voids being substantially filled by a binder, wherein the fibers exhibit a first acoustical impedance and said matrix exhibits a second, lower acoustical impedance, wherein the first acoustical impedance and the second acoustical impedance are selected such that acoustical energy received by said composite is subject to scattering by said fibers and attenuation in said matrix; and
    whereby the acoustic isolator reduces the reflection of rear-propagated acoustic energy from the support structure to the pulse generator, so as to reduce undesirable ultrasound display artifacts.

13. The acoustic transducer of claim 12, wherein the fibers are selected from a group of fiber materials consisting of: metallic fibers; metal-on-metal fibers; metal-clad fibers; ceramic fibers, and filamentary materials.

14. The acoustic transducer of claim 12, wherein said binder is provided in the matrix by a technique selected from the group consisting of: injection, pultrusion, compression molding, slip-forming, and vacuum-impregnation.

15. The acoustic transducer of claim 12, wherein said binder is selected from a group of binder materials consisting of: thermoplastic polymers and thermosetting resins.

16. The acoustic transducer of claim 12, wherein said preform comprises spaced fibers arranged according to a predetermined fiber architecture, said fiber architecture being selected from the group consisting of: linear fiber system; planar fiber system, and integrated fiber system.

17. The acoustic transducer of claim 16, wherein said preform further comprises stacked layers of macroporous metallic mesh sheets.

18. The acoustic transducer of claim 17, wherein said mesh sheets comprise tungsten filaments.

19. The acoustic transducer of claim 1, wherein said matrix further comprises an additive having a physical characteristic selected from a group consisting of: thermally conductive and electrically conductive.

20. A method for constructing an electroacoustic transducer, comprising the steps of:
    constructing an acoustic isolator to include a composite formed of a preform and a matrix, wherein the preform includes fibers arranged in spaced relationship so as to define a plurality of voids, said voids being substantially filled by a binder, wherein the fibers exhibit a first acoustical impedance and said matrix exhibits a second, lower acoustical impedance, wherein the first acoustical impedance and the second acoustical impedance are selected such that acoustical energy received by said composite is subject to scattering by said fibers and attenuation in said matrix;

constructing a base having a support structure, the acoustic absorber, and an acoustic isolator; and constructing an acoustic pulse generator having both a front application face and a rear face, wherein the acoustic absorber is attached to the rear face of the pulse generator and the acoustic isolator is positioned between the acoustic absorber and the support structure;

wherein the acoustic isolator is operable to reduce the reflection of rear-propagated acoustic energy from the support structure to the pulse generator, so as to reduce undesirable ultrasound display artifacts.

* * * * *